US00PP30433P3

(12) United States Plant Patent
Stone et al.

(10) Patent No.: US PP30,433 P3
(45) Date of Patent: Apr. 23, 2019

(54) FEMALE ASPARAGUS PLANT NAMED 'FCE4'

(50) Latin Name: *Asparagus officinalis*
Varietal Denomination: FCE4

(71) Applicant: The Regents of the University of California, Oakland, CA (US)

(72) Inventors: Neil K. Stone, Temecula, CA (US); Mikeal L. Roose, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 15/731,450

(22) Filed: Jun. 9, 2017

(65) Prior Publication Data

US 2018/0359894 P1 Dec. 13, 2018

(51) Int. Cl.
*A01H 5/04* (2018.01)
*A01H 6/12* (2018.01)

(52) U.S. Cl.
USPC ..... Plt./260
CPC ..... *A01H 6/12* (2018.05)

(58) Field of Classification Search
USPC ..... Plt./258, 260
See application file for complete search history.

(56) References Cited

PUBLICATIONS

Asparagus: Variety Evaluation and Weed management Trials in San Joaquin County, 2009 Reserach Progress Report. 2009. University of California Cooperative Extension. 9 pages. (Year: 2009).*

* cited by examiner

*Primary Examiner* — Susan McCormick Ewoldt
*Assistant Examiner* — Karen M Redden
(74) *Attorney, Agent, or Firm* — Kilpatrick Townsend & Stockton LLP

(57) ABSTRACT

This invention is a new and distinctive female *asparagus* plant called 'FCE4'.

2 Drawing Sheets

Latin name of the genus and species: *Asparagus officinalis.*

Variety denomination: The variety denomination is 'FCE4'.

BACKGROUND OF THE INVENTION

*Asparagus* is a dioecious species with individual plants being either male or female. *Asparagus* cultivars that have been most commonly used for fresh market green *asparagus* in the major growing regions of California include, 'Atlas' (unpatented), 'Grande' (unpatented), 'Ida Lea' (unpatented), 'UC157' (unpatented), and 'DePaoli' (US PVP Certificate No. 200700127). These cultivars are all produced from crossing a genetically unique male clone with a genetically unique female clone to produce F1 seed.

BRIEF SUMMARY OF THE INVENTION

'FCE4' is a new and genetically distinct female *asparagus* clone that is used to produce *asparagus* cultivars that have commercially desirable traits. The closest cultivar to 'FCE4' known to the inventor is an unreleased female *asparagus* clone 'F600' (unpatented). 'FCE4' can be distinguished from 'F600' by its ability to provide a hybrid *asparagus* cultivar that has spears of a greater weight when crossed with male *asparagus* 'M256' (U.S. Plant Pat. No. 20,629) compared to the weight of the spears from the hybrid cultivar resulting from crossing 'F600' with 'M256'.

DETAILED DESCRIPTION OF THE INVENTION

Pedigree 'FCE4' was selected as a single plant in 1999 from a cross between female *asparagus* clone 'F109' (U.S. Plant Pat. No. 4,677) and male *asparagus* clone 'EC2' (unpatented) and propagated by tissue culture. 'FCE4' was first asexually produced in May 2008 in Riverside, Calif., USA. 'FCE4' was selected based on plant vigor, height to the first branch, and its ability to produce a large number of high quality spears. These three selection criteria were applied to 242 plants from the population produced from the cross, 'F109' x 'EC2'. The combination of all three criteria allowed 'FCE4' to stand out as a clone for selection and further testing as a parent.

'FCE4' has a larger spear diameter compared to either the female parent 'F109' or male parent 'EC2'; and a greater distance between nodes when compared to either parent. The height to the first branch is also greater for 'FCE4' compared to either 'F109' or 'EC2'. 'FCE4' was first asexually produced in May 2008 in Riverside, Calif., USA.

Cultivation 'FCE4' can be clonally propagated by crown division. The distinguishing characteristics of 'FCE4' are stable and reproduce true to type in successive generations of asexual reproduction in Riverside, Calif., USA, and in test trials in San Gerardo, Chile. 'FCE4' is usually grown in isolated plantings of clonally propagated plants along with a male clone to produce F1 seeds. Recommended cultural practices for 'FCE4' are similar to those of other *asparagus* plantings for seed production. Plantings can be established using 8-week old seedling transplants or 1-year-old crowns. Performance can be good on soils with low (Riverside, Calif.) or high (Delta regions of California) organic content. Rust and *asparagus* aphid should be controlled with spray regimes.

'FCE4' emerges in the spring earlier than most other *asparagus* clones it has been grown with.

Figure 1:
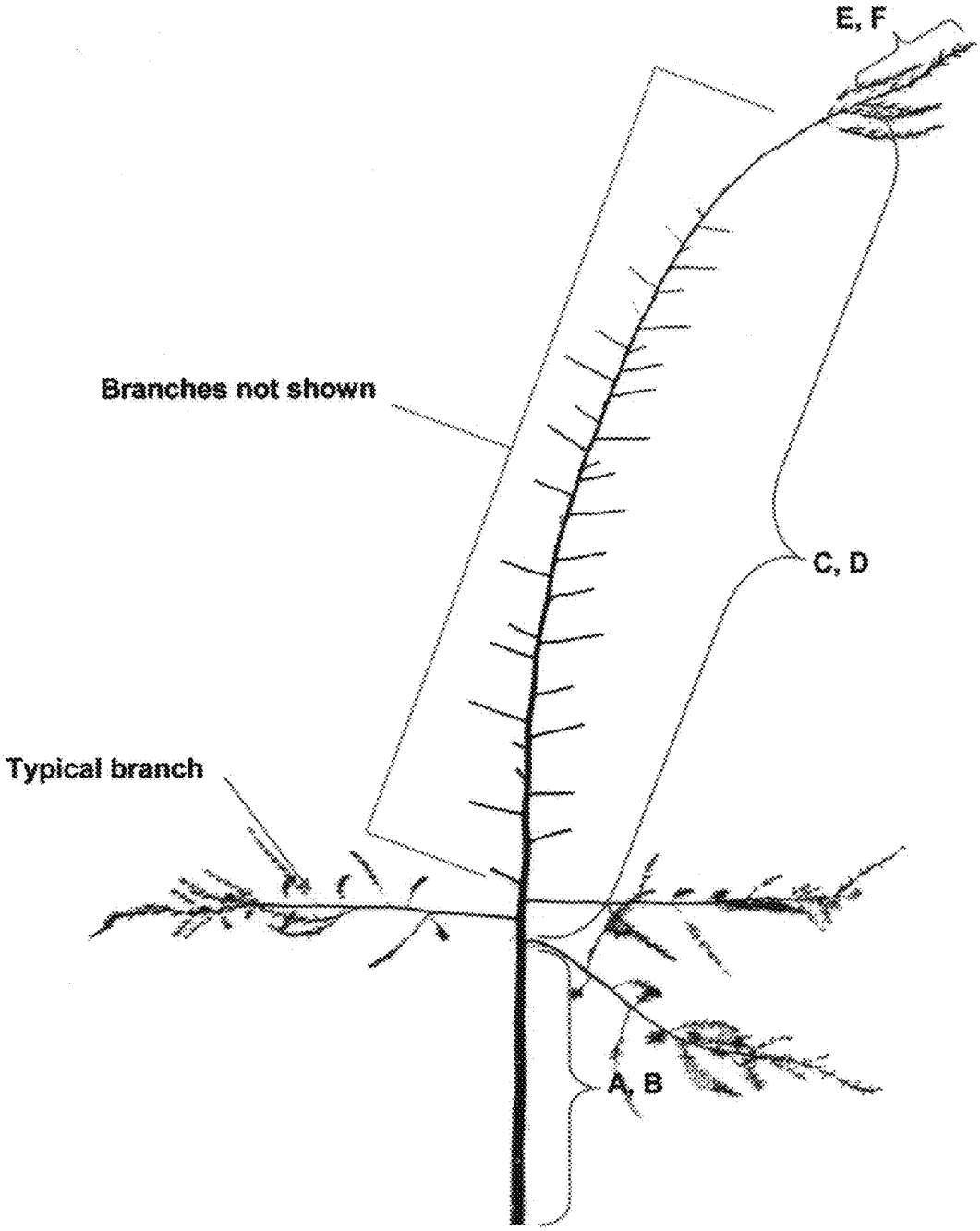
FIG. 1 provides an illustration of a typical stalk from an *asparagus* plant. The Figure illustrates the relative positions on the plant and the source of the data presented below. References are made with the use of brackets and letters, the same letters which are also listed in parentheses under the stalk data.
Figure 2:
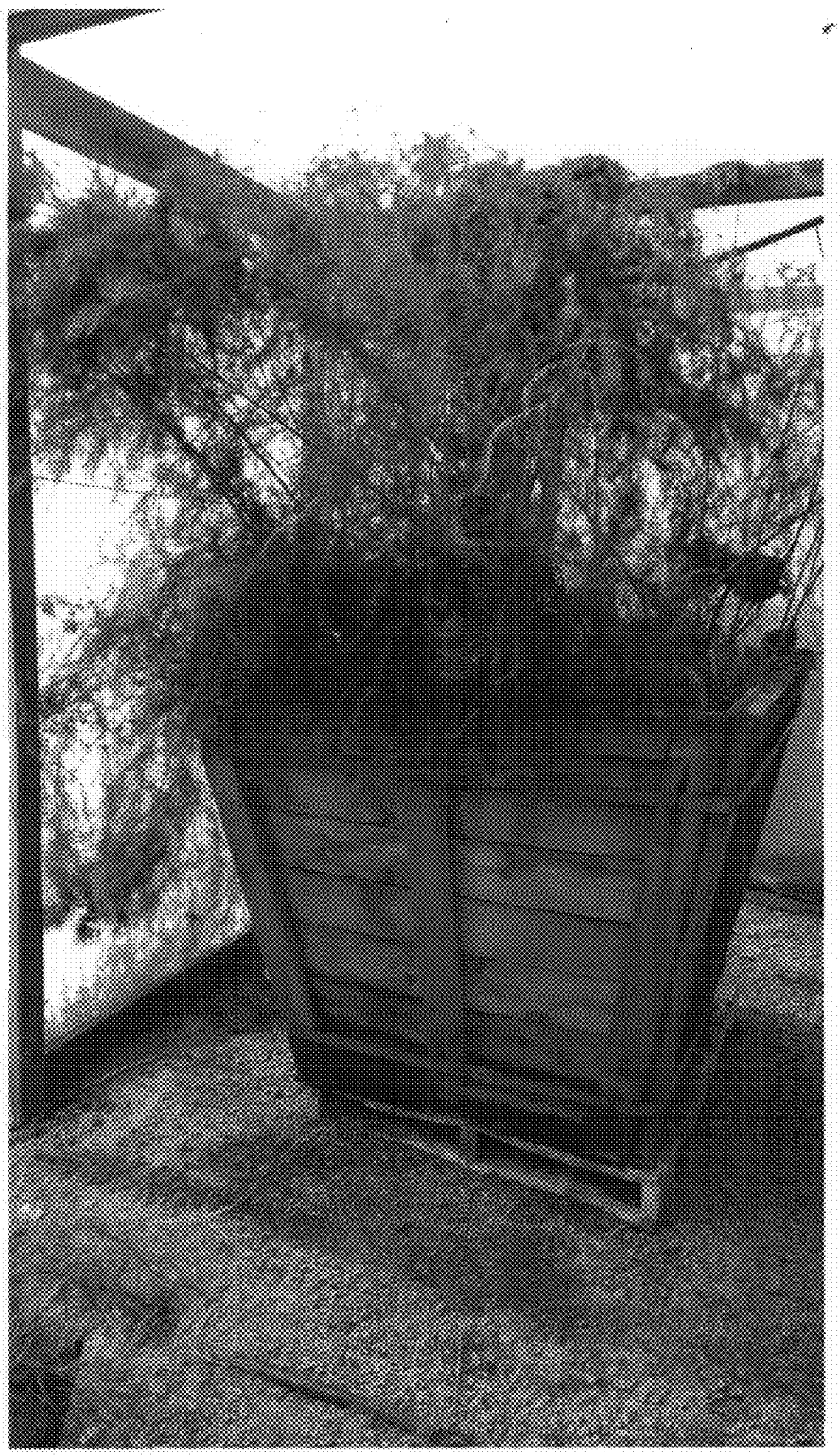
FIG. 2 shows typical foliage of 'FCE4'. The photograph depicts a four year old 'FCE4' plant in a greenhouse at Riverside, Calif.

Plant characteristics: The attached photograph, FIG. 1, illustrates the relative positions on the plant and the source of the data presented below. References are made with the use of brackets and letters, the same letters which are also listed in parentheses under the stalk data. Typical foliage of 'FCE4' is shown in FIG. 2. The plant observed for the detailed botanical description was approximately 8 months old and growing in a greenhouse with full sunlight and daytime temperatures below 85 degrees Fahrenheit and nighttime temperatures above 60 degrees Fahrenheit. The plant was in a 8.25 in.×9 in. diameter pot filled with soil that was approximately 50% sand, 50% peat moss. The following measurements were obtained from the longest stalk and are the mean value of measurements on five separate clones unless otherwise indicated. The colors presented below refer to colors in The Royal Horticultural Society Colour Chart (2001) and are the most common colors observed among the plants measured.

Stalk description:

*Number of nodes below the first branch* (*A*).—22.2.

*Number of cm from crown to the first branch* (*B*).—37.

*Number of branches* (*C*).—36.2.

*Number of cm between first and last branch* (*D*).—43.9.

*Internode length in cm between branches* (*D*/(*C*-1)).—1.25.

*Number of cladophyll nodes beyond the last branch* (*E*).—28.0.

*Number of cm beyond the last branch* (*F*).—7.9.

*Internode length in cm beyond the last branch* (*F*/(*E*-1)).—0.29.

*Largest stalk diameter in mm.*—9.86.

*Mean diameter of three largest stalks in mm.*—9.83.

*Number of stalks.*—7.0.

*Stalk vigor index* (*stalk number*)(*mean diameter*)$^2$.—674.08.

*Mature stalk color, bloom removed.*—144B.

Flower description:

*Tepal tip color* (*four plants*).—Green-yellow 1D.

*Tepal apex outer surface margin color.*—Green-yellow 1D.

*Tepal apex inner surface margin color.*—Green-yellow 1D.

*Tepal apex outer surface middle.*—Yellow-green 146C.

*Tepal apex inner surface middle.*—Yellow-green 146C.

*Tepal base outer surface.*—Yellow-green 146C.

*Tepal base outer surface middle.*—Yellow-green 146C.

*Tepal base inner surface middle.*—Yellow-green 146C.

*Tepal number and configuration.*—Six in number, imbricate in two whorls forming campanulate corolla at anthesis, syntepalous for lower 1 mm, with separate tepals above.

*Tepal shape.*—Elliptical, but slightly wider toward apex.

*Tepal base.*—Cuneate, margin entire.

*Flower length in mm.*—4.33.

*Flower width at midpoint in mm.*—1.98. Flowers typically in leaf axils, solitary or in pairs.

*Sepals.*—The perianth of 'FCE4' consists of tepals, sepals, and petals, which are indistinguishable from each other.

Cladophyll description:

*Number per node.*—5.4.

*Length in mm.*—19.92.

*Width in mm.*—0.22.

*Shape.*—Linear, filiform, needle-like, round in cross.

*Base.*—Cuneate, margin entire.

*Adaxial surface color.*—Green 137B.

*Abaxial surface color.*—Green 137B.

Bract (true leaf) description: Rudimentary, scale-like, triangular, membranous near margin. Small appendage hanging from idle of dorsal side closest to stem. Entire margins, acute apex.

*Length.*—12.0 mm, Width: 6.4 mm.

*Attitude of bracts.*—Closely adpessed.

Peduncle:

*Length.*—13.8 mm.

*Diameter.*—0.3 mm; 0.5 mm diameter joint between ½ to ⅔ of the length form the axil.

*Color.*—Yellow-green 146A.

Female reproductive organs:

*Gynoecium.*—Fused, single styled. Tricarpellate with visible longitudinal sutures along ovary and style. Ovary sessile, obovate, 2.0 mm long, 1.5 mm wide at anthesis.

*Ovule number, shape.*—Six, circular.

*Ovary color.*—Yellow-green 144A.

*Style.*—Tripartite, fused into one, filiform, 1.3 mm; 0.2 mm wide at midpoint. Papillate on adaxial surface, recurved to horizontal. Color: Green-white 157D.

*Stigma.*—Lobed, trifid 0.6 mm side. Color: Green-white 157D.

Fruit description:

*Shape and texture.*—Round, smooth, fleshy with walls forming three locules, each locule containing up to 2 seeds.

*Size of berry.*—6-10 mm in width.

*Color* (*ripe fruit*).—Orange-red 32A.

What is claimed is:

1. A new and distinct female *asparagus* plant having the characteristics essentially as described and illustrated herein.

* * * * *